(12) United States Patent
Wood, Jr. et al.

(10) Patent No.: US 8,652,064 B2
(45) Date of Patent: Feb. 18, 2014

(54) SAMPLING CIRCUIT FOR MEASURING ANALYTES

(75) Inventors: Lockett E. Wood, Jr., Lyons, CO (US);
Ron J. Kadlac, Longmont, CO (US);
John Andrew Battista, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 1016 days.

(21) Appl. No.: 12/242,887

(22) Filed: Sep. 30, 2008

(65) Prior Publication Data
US 2010/0081955 A1 Apr. 1, 2010

(51) Int. Cl.
*A61B 5/097* (2006.01)
*A61B 5/08* (2006.01)

(52) U.S. Cl.
USPC .......................................... 600/532

(58) Field of Classification Search
None
See application file for complete search history.

(56) References Cited

U.S. PATENT DOCUMENTS

| | | | |
|---|---|---|---|
| 4,267,827 A | 5/1981 | Rauscher et al. |
| 4,752,089 A | 6/1988 | Carter |
| 4,770,168 A | 9/1988 | Rusz et al. |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,228,434 A | 7/1993 | Fishman |
| 5,237,987 A | 8/1993 | Anderson et al. |
| 5,271,389 A | 12/1993 | Isaza et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,307,795 A | 5/1994 | Whitwam et al. |
| 5,319,540 A | 6/1994 | Isaza et al. |
| 5,325,861 A | 7/1994 | Goulding |
| 5,333,606 A | 8/1994 | Schneider et al. |

(Continued)

FOREIGN PATENT DOCUMENTS

EP 3416291 3/1984
EP 4312431 4/1993

(Continued)

OTHER PUBLICATIONS

7200 Series Ventilator, Options, and Accessories: Operators Manual. Nellcor Puritan Bennett, Part No. 22300 A, Sep. 1990, pp. 1-196.

(Continued)

*Primary Examiner* — Shanon A Foley (57) ABSTRACT

This disclosure describes an apparatus and method for measuring analytes in exhaled air. The device contains an inlet through which exhaled air is received. A tube, having a number of different paths running throughout the device, is coupled to the inlet which enables the exhaled air to be re-circulated through the device. At least one portion of the tube is configured in a non-linear fashion. This particular portion of the tube may be used to temporarily store a sample of the exhaled air. The device also contains a converter configured to partially convert an analyte in the exhaled breath from a first state to a second state as the exhaled air is being re-circulated. An analyte sensor is also included to measure the levels of the converted analyte in the exhaled breath.

13 Claims, 3 Drawing Sheets

(56) References Cited

U.S. PATENT DOCUMENTS

| | | |
|---|---|---|
| 5,339,807 A | 8/1994 | Carter |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,485,835 A | 1/1996 | Vande Streek et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,218 A | 7/1996 | Kreb |
| 5,531,221 A | 7/1996 | Power |
| 5,533,512 A | 7/1996 | Novotny et al. |
| 5,542,415 A | 8/1996 | Brady |
| 5,544,674 A | 8/1996 | Kelly |
| 5,549,106 A | 8/1996 | Gruenke et al. |
| 5,558,083 A | 9/1996 | Bathe et al. |
| 5,579,774 A | 12/1996 | Miller et al. |
| 5,596,984 A | 1/1997 | O'Mahoney et al. |
| 5,630,411 A | 5/1997 | Holscher |
| 5,632,270 A | 5/1997 | O'Mahoney et al. |
| 5,645,048 A | 7/1997 | Brodsky et al. |
| 5,651,358 A | 7/1997 | Briend et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,697,364 A | 12/1997 | Chua et al. |
| 5,715,812 A | 2/1998 | Deighan et al. |
| 5,720,277 A | 2/1998 | Olsson et al. |
| 5,732,693 A | 3/1998 | Bathe et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,836,300 A | 11/1998 | Mault |
| 5,839,433 A | 11/1998 | Higenbottam |
| 5,857,460 A | 1/1999 | Popitz |
| 5,864,938 A | 2/1999 | Gansel et al. |
| 5,865,168 A | 2/1999 | Isaza |
| 5,871,009 A | 2/1999 | Rydgren et al. |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,089,229 A | 7/2000 | Bathe et al. |
| 6,099,481 A | 8/2000 | Daniels et al. |
| 6,109,260 A | 8/2000 | Bathe |
| 6,116,240 A | 9/2000 | Merrick et al. |
| 6,116,464 A | 9/2000 | Sanders |
| 6,123,072 A | 9/2000 | Downs |
| 6,123,073 A | 9/2000 | Schlawin et al. |
| 6,125,846 A | 10/2000 | Bathe et al. |
| 6,131,571 A | 10/2000 | Lampotang et al. |
| 6,135,105 A | 10/2000 | Lampotang et al. |
| 6,135,106 A | 10/2000 | Dirks et al. |
| 6,135,107 A | 10/2000 | Mault |
| 6,142,147 A | 11/2000 | Head et al. |
| 6,142,150 A | 11/2000 | O'Mahoney et al. |
| 6,161,539 A | 12/2000 | Winter |
| 6,164,276 A | 12/2000 | Bathe et al. |
| 6,179,784 B1 | 1/2001 | Daniels et al. |
| 6,200,271 B1 | 3/2001 | Kück et al. |
| 6,210,342 B1 | 4/2001 | Kück et al. |
| 6,220,245 B1 | 4/2001 | Takabayashi et al. |
| 6,236,041 B1 | 5/2001 | Donnerhack et al. |
| 6,238,351 B1 | 5/2001 | Orr et al. |
| 6,258,038 B1 | 7/2001 | Haryadi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,439,229 B1 | 8/2002 | Du et al. |
| 6,439,234 B1 | 8/2002 | Curti et al. |
| 6,467,478 B1 | 10/2002 | Merrick et al. |
| 6,471,658 B1 | 10/2002 | Daniels et al. |
| 6,536,429 B1 | 3/2003 | Pavlov et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,581,592 B1 | 6/2003 | Bathe et al. |
| 6,581,599 B1 | 6/2003 | Stenzler |
| 6,616,615 B2 | 9/2003 | Mault et al. |
| 6,622,726 B1 | 9/2003 | Du |
| 6,629,934 B2 | 10/2003 | Mault et al. |
| 6,644,310 B1 | 11/2003 | Delache et al. |
| 6,648,831 B2 | 11/2003 | Orr et al. |
| 6,648,832 B2 | 11/2003 | Orr et al. |
| 6,655,385 B1 | 12/2003 | Curti et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,758,214 B2 | 7/2004 | Fine et al. |
| 6,761,167 B1 | 7/2004 | Nadjafizadeh et al. |
| 6,761,168 B1 | 7/2004 | Nadjafizadeh et al. |
| 6,786,217 B2 | 9/2004 | Stenzler |
| 6,814,074 B1 | 11/2004 | Nadjafizadeh et al. |
| 6,860,266 B2 | 3/2005 | Blike |
| 6,866,040 B1 | 3/2005 | Bourdon |
| 6,871,645 B2 | 3/2005 | Wartman et al. |
| 6,884,222 B1 | 4/2005 | Braig |
| 6,935,336 B2 | 8/2005 | Lurie et al. |
| 6,938,618 B2 | 9/2005 | Lurie et al. |
| 6,955,651 B2 | 10/2005 | Kück et al. |
| 6,960,854 B2 | 11/2005 | Nadjafizadeh et al. |
| 6,997,880 B2 | 2/2006 | Carlebach et al. |
| 7,018,340 B2 | 3/2006 | Jaffe et al. |
| 7,024,235 B2 | 4/2006 | Melker et al. |
| 7,025,869 B2 | 4/2006 | Fine et al. |
| 7,036,504 B2 | 5/2006 | Wallace et al. |
| 7,040,313 B2 | 5/2006 | Fine et al. |
| 7,070,566 B2 | 7/2006 | Medero et al. |
| 7,070,569 B2 | 7/2006 | Heinonen et al. |
| 7,070,570 B2 | 7/2006 | Sanderson et al. |
| 7,077,131 B2 | 7/2006 | Hansen |
| RE39,225 E | 8/2006 | Isaza et al. |
| 7,108,666 B2 | 9/2006 | Stenzler |
| 7,117,438 B2 | 10/2006 | Wallace et al. |
| 7,152,604 B2 | 12/2006 | Hickle et al. |

(56) References Cited

U.S. PATENT DOCUMENTS

| | | | |
|---|---|---|---|
| 7,185,649 B2 | 3/2007 | Lurie | |
| 7,195,012 B2 | 3/2007 | Lurie | |
| 7,207,947 B2 | 4/2007 | Koh et al. | |
| 7,210,480 B2 | 5/2007 | Lurie et al. | |
| 7,225,022 B2 | 5/2007 | Anderson et al. | |
| 7,270,126 B2 | 9/2007 | Wallace et al. | |
| 7,273,050 B2 | 9/2007 | Wei | |
| 7,275,542 B2 | 10/2007 | Lurie et al. | |
| 7,335,181 B2 | 2/2008 | Miller et al. | |
| 7,369,757 B2 | 5/2008 | Farbarik | |
| 7,370,650 B2 | 5/2008 | Nadjafizadeh et al. | |
| 7,387,123 B2 | 6/2008 | DeSilva et al. | |
| 7,425,201 B2 | 9/2008 | Euliano et al. | |
| 7,428,902 B2 | 9/2008 | Du et al. | |
| 7,438,072 B2 | 10/2008 | Izuchukwu | |
| 7,460,959 B2 | 12/2008 | Jafari | |
| 7,487,773 B2 | 2/2009 | Li | |
| 7,588,543 B2 | 9/2009 | Euliano et al. | |
| 7,654,802 B2 | 2/2010 | Crawford, Jr. et al. | |
| 7,694,677 B2 | 4/2010 | Tang | |
| 7,717,113 B2 | 5/2010 | Andrieux | |
| 7,784,461 B2 | 8/2010 | Figueiredo et al. | |
| 7,823,588 B2 | 11/2010 | Hansen | |
| 7,846,739 B2 * | 12/2010 | von Bahr et al. | 436/116 |
| 7,855,716 B2 | 12/2010 | McCreary et al. | |
| 7,891,354 B2 | 2/2011 | Farbarik | |
| 7,893,560 B2 | 2/2011 | Carter | |
| 7,984,714 B2 | 7/2011 | Hausmann et al. | |
| 7,992,557 B2 | 8/2011 | Nadjafizadeh et al. | |
| 8,001,967 B2 | 8/2011 | Wallace et al. | |
| 8,021,310 B2 | 9/2011 | Sanborn et al. | |
| 8,181,648 B2 | 5/2012 | Perine et al. | |
| 8,210,173 B2 | 7/2012 | Vandine | |
| 8,210,174 B2 | 7/2012 | Farbarik | |
| 8,272,379 B2 | 9/2012 | Jafari et al. | |
| 8,272,380 B2 | 9/2012 | Jafari et al. | |
| 8,302,600 B2 | 11/2012 | Andrieux et al. | |
| 8,302,602 B2 | 11/2012 | Andrieux et al. | |
| 2002/0029003 A1 | 3/2002 | Mace et al. | |
| 2002/0069877 A1 | 6/2002 | Villareal et al. | |
| 2002/0087057 A1 | 7/2002 | Lovejoy et al. | |
| 2003/0045807 A1 | 3/2003 | Daniels, II et al. | |
| 2003/0062040 A1 | 4/2003 | Lurie et al. | |
| 2003/0070678 A1 | 4/2003 | Wartman et al. | |
| 2003/0106553 A1 | 6/2003 | Vanderveen | |
| 2003/0106554 A1 | 6/2003 | De Silva et al. | |
| 2003/0225339 A1 | 12/2003 | Orr et al. | |
| 2004/0040560 A1 | 3/2004 | Euliano et al. | |
| 2004/0045552 A1 | 3/2004 | Curti et al. | |
| 2004/0082872 A1 * | 4/2004 | von Bahr et al. | 600/532 |
| 2004/0116784 A1 | 6/2004 | Gavish | |
| 2004/0133116 A1 * | 7/2004 | Abraham-Fuchs et al. | 600/532 |
| 2004/0144383 A1 | 7/2004 | Thomas et al. | |
| 2004/0254482 A1 | 12/2004 | Anderson et al. | |
| 2005/0039748 A1 | 2/2005 | Andrieux | |
| 2005/0109340 A1 | 5/2005 | Tehrani | |
| 2005/0112325 A1 | 5/2005 | Hickle | |
| 2005/0137645 A1 | 6/2005 | Voipio et al. | |
| 2005/0139212 A1 | 6/2005 | Bourdon | |
| 2005/0139213 A1 | 6/2005 | Blike | |
| 2005/0215844 A1 | 9/2005 | Ten Eyck et al. | |
| 2005/0217671 A1 | 10/2005 | Fisher et al. | |
| 2005/0247311 A1 | 11/2005 | Vacchiano et al. | |
| 2005/0251214 A1 | 11/2005 | Parascandola et al. | |
| 2005/0284476 A1 | 12/2005 | Blanch et al. | |
| 2005/0284484 A1 | 12/2005 | Curti et al. | |
| 2006/0129054 A1 | 6/2006 | Orr et al. | |
| 2006/0189880 A1 | 8/2006 | Lynn et al. | |
| 2006/0225737 A1 | 10/2006 | Iobbi | |
| 2006/0231098 A1 | 10/2006 | Downie et al. | |
| 2006/0249151 A1 | 11/2006 | Gambone | |
| 2006/0253038 A1 | 11/2006 | Kuck et al. | |
| 2007/0017515 A1 | 1/2007 | Wallace et al. | |
| 2007/0034208 A1 | 2/2007 | Roehl et al. | |
| 2007/0044799 A1 | 3/2007 | Hete et al. | |
| 2007/0053992 A1 | 3/2007 | Abraini et al. | |
| 2007/0062531 A1 | 3/2007 | Fisher et al. | |
| 2007/0068518 A1 | 3/2007 | Urias et al. | |
| 2007/0073170 A1 | 3/2007 | Danehorn et al. | |
| 2007/0077200 A1 | 4/2007 | Baker | |
| 2007/0107728 A1 | 5/2007 | Ricciardelli et al. | |
| 2007/0129666 A1 | 6/2007 | Barton et al. | |
| 2007/0149891 A1 | 6/2007 | George et al. | |
| 2007/0151561 A1 | 7/2007 | Laurila | |
| 2007/0157931 A1 | 7/2007 | Parker et al. | |
| 2007/0181126 A1 | 8/2007 | Tolmie et al. | |
| 2007/0221222 A1 | 9/2007 | Lurie | |
| 2007/0225612 A1 | 9/2007 | Mace et al. | |
| 2007/0227537 A1 | 10/2007 | Bemister et al. | |
| 2007/0232951 A1 | 10/2007 | Euliano et al. | |
| 2007/0255160 A1 | 11/2007 | Daly | |
| 2007/0272243 A1 | 11/2007 | Sherman et al. | |
| 2007/0277823 A1 | 12/2007 | Ai-Ali et al. | |
| 2007/0284361 A1 | 12/2007 | Nadjafizadeh et al. | |
| 2008/0029091 A1 | 2/2008 | Mullner | |
| 2008/0039735 A1 | 2/2008 | Hickerson | |
| 2008/0053441 A1 | 3/2008 | Gottlib et al. | |
| 2008/0072896 A1 | 3/2008 | Setzer et al. | |
| 2008/0072902 A1 | 3/2008 | Setzer et al. | |
| 2008/0078390 A1 | 4/2008 | Milne et al. | |
| 2008/0083644 A1 | 4/2008 | Janbakhsh et al. | |
| 2008/0087284 A1 | 4/2008 | Krueger et al. | |
| 2008/0092894 A1 | 4/2008 | Nicolazzi et al. | |
| 2008/0097234 A1 | 4/2008 | Nicolazzi et al. | |
| 2008/0194980 A1 | 8/2008 | Gisolf et al. | |
| 2008/0202526 A1 | 8/2008 | Heinonen | |
| 2008/0230065 A1 | 9/2008 | Heinonen | |
| 2008/0236581 A1 | 10/2008 | Rantala et al. | |
| 2008/0236582 A1 | 10/2008 | Tehrani | |
| 2008/0275340 A1 | 11/2008 | Beach et al. | |
| 2008/0295839 A1 | 12/2008 | Habashi | |
| 2010/0011307 A1 | 1/2010 | Desfossez et al. | |
| 2010/0024820 A1 | 2/2010 | Bourdon | |
| 2010/0071689 A1 | 3/2010 | Thiessen | |
| 2010/0071695 A1 | 3/2010 | Thiessen | |
| 2010/0071696 A1 | 3/2010 | Jafari | |
| 2010/0078017 A1 | 4/2010 | Andrieux et al. | |
| 2010/0078026 A1 | 4/2010 | Andrieux et al. | |
| 2010/0081119 A1 | 4/2010 | Jafari et al. | |
| 2010/0081955 A1 | 4/2010 | Wood, Jr. et al. | |

FOREIGN PATENT DOCUMENTS

| | | |
|---|---|---|
| EP | 19701617 | 1/1997 |
| FR | 2850874 | 8/2004 |
| WO | WO9710869 | 3/1997 |
| WO | WO9831282 | 7/1998 |
| WO | WO2008012350 | 1/2008 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operators and Technical Reference Manual. Ventilator System, Nellcor Puritan Bennett, Part No. 4-075609-00, Rev. G, Oct. 2006, pp. 1-424.

* cited by examiner

SAMPLING CIRCUIT FOR MEASURING ANALYTES

BACKGROUND

The diagnosis of diseases through analysis of human breath has long been practiced in medicine. For example, by smell alone, various volatile components of breath such as acetone, ammonia or sulfur compounds can be detected and provide information used to evaluate conditions such as diabetes, liver impairment and kidney dysfunction. Gas chromatography and mass spectrometry also have been applied to evaluate exposure to toxic substances, liver disease and lung cancer.

Thus, the measurement of exhaled substances may be useful as a diagnostic and prognostic tool for a wide variety of medical conditions. Often, it is of interest when assessing pulmonary function to measure one or more of a variety of exhaled substances. These include endogenous gases (i.e., oxygen, carbon dioxide and nitric oxide), exogenous gases used to test pulmonary diffusing capacity (i.e., carbon monoxide, acetylene, argon and helium), volatile substances (i.e., ethane and pentane) and non-volatile substances (i.e., proteins such as surfactants, DNA and hydrogen peroxide) often found by sampling the liquid present in exhaled breath (i.e., breath condensate).

One exhaled substance of particular interest is exhaled endogenous nitric oxide ("NO"). Nitric oxide is now known to be a central mediator in biological systems and, therefore, endogenous exhaled nitric oxide is thus potentially of interest in the diagnosis and monitoring of pulmonary function and various pulmonary diseases. Nitric oxide can be measured in the exhaled breath of animal and human subjects and shows particular promise as a diagnostic tool useful in evaluating inflammatory airway diseases, in particular bronchial asthma, and also in evaluating bronchiectasis and lung transplant rejection and other pulmonary conditions.

For example, asthmatic patients have relatively high exhaled NO levels as compared to normal subjects and these levels decrease rapidly after the institution of anti-inflammatory therapy. Thus, measuring exhaled NO in conjunction with existing tests may aid in the diagnosis and assessment of asthma, and also be an index of the response to therapy, or patient compliance in therapy. In view of the importance of asthma as a major health problem, the commercial potential is great for tests that can help diagnose asthma severity and ascertain the response to therapy.

SUMMARY

This disclosure describes an apparatus and method for measuring analytes in exhaled air. As discussed in greater detail below, the disclosure describes a monitoring device having an inlet tube though which a patient using the device, inhales and exhales air. The device contains a tube having a number of different paths running throughout the device, with various paths supplying the exhaled air to different components. According to an embodiment, at least one portion of the tube is configured in a non-linear fashion. This particular portion of the tube may be used to temporarily store a sample of the exhaled air. Alternatively, the tube may be straight. In either embodiment, the tube has uniform diameter so ambient air that is drawn into the tube is minimally mixed with the sample. A pump is also included in the device and is configured to circulate the exhaled air through the tube. The device also contains a converter configured to partially convert an analyte in the exhaled breath from a first state to a second state. The tube and corresponding paths are arranged in such a manner whereby the exhaled air can be re-circulated and passed through the converter multiple times. An analyte sensor is also included to measure the levels of the converted analyte in the exhaled breath. One or more valves may also be included in the device to direct the flow of the exhaled air through the device to the various components.

In another embodiment, an apparatus is disclosed for measuring an analyte in exhaled air. In an embodiment the apparatus contains an inlet through which the exhaled air is received. A tube, having a number of different paths that provide the exhaled air to various components of the device, may be coupled to the inlet. One or more valves are coupled to the tube and control the flow of the exhaled air to the different paths of the tube. The tube may also contain a non-linear tube portion that is used to temporarily store a sample of the exhaled air. Alternatively, the tube may also be straight. In either embodiment, the tube has a relatively small diameter which mostly prevents ambient air from mixing with the sample air. The device also includes a pump that is configured to control the flow of the exhaled air through the device. In an embodiment the device contains a converter configured to receive the exhaled air at least a first time and a second time. The first time the exhaled air is received, the converter partially converts an analyte contained in the exhaled air from a first state to a second state. When the air has been re-circulated and passes through the converter a second time, the analyte is further converted from the first state to the second state.

Also disclosed herein is a method for measuring an analyte in exhaled air. According to an embodiment, exhaled air is received into an inlet. Once the air is received, the air is circulated through a tube having a plurality of paths. One portion of the tube is arranged in a non-linear configuration into which the exhaled air may flow and be temporarily stored. The exhaled air is then passed through a converter, which partially converts an analyte in the exhaled air from a first state to a second state. The converted analyte is then passed to an analyte sensor.

In yet another embodiment an apparatus is disclosed having an inlet through which exhaled air is received into the device. A tube is coupled to the inlet, the tube having a non-linear portion configured to store the exhaled air. The device also contains an analyte sensor for measuring an analyte contained in the exhaled air.

Although the examples and claims herein refer to converting an analyte from a first state to a second state, the term state as used herein means converting one compound into a second compound. For example, the converter may be configured to convert nitric oxide ("NO") to nitrogen dioxide ("$NO_2$"). Although this specific implementation is set forth, it is contemplated that a variety of other analytes and components present in exhaled breath can be converted from one state to another (if necessary) and measured by the disclosed apparatus. Such analytes may include, but are not limited to, carbon dioxide, oxygen, nitrogen, nitrogen dioxide, hydrogen peroxide, proteins, surfactants, DNA, acetone, ammonia, sulfur compounds, acetylene, carbon monoxide, ethane and pentane. Although the aforementioned analytes may not need to be converted from a first state to a second state, the device as described herein may be configured to bypass the conversion component and send the analyte directly to an analyte sensor.

These and various other features as well as advantages which characterize the disclosed systems and methods will be apparent from a reading of the following detailed description and a review of the associated drawings. Additional features of the device and methods described herein are set forth in the description which follows, and in part will be apparent from the description, or may be learned by practice of the technology. The benefits and features will be realized and attained by the structure particularly pointed out in the written description and claims as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

This disclosure describes an apparatus and method for measuring analytes in exhaled air. As discussed in greater detail below, the disclosure describes a monitoring device having an inlet tube though which a patient using the device, inhales and exhales air. The device contains a tube having a number of different paths running throughout the device, with various paths supplying the exhaled air to different components. According to an embodiment, at least one portion of the tube is configured in a non-linear fashion. This particular portion of the tube may be used to temporarily store a sample of the exhaled air. A pump is also included in the device and is configured to circulate the exhaled air through the tube. The device also contains a converter configured to partially convert an analyte in the exhaled breath from a first state to a second state. The tube and corresponding paths are arranged in such a manner whereby the exhaled air can be re-circulated and passed through the converter multiple times. An analyte sensor is also included to measure the levels of the converted analyte in the exhaled breath. One or more valves may also be included in the device to direct the flow of the exhaled air through the device to the various components.

Although the device and method described below are in the context of an apparatus used for converting nitric oxide in exhaled air to nitrogen dioxide, it is contemplated that such an apparatus as described herein may be implemented to detect, measure and convert (if necessary) a variety of analytes present in exhaled breath.

Figure 1A:
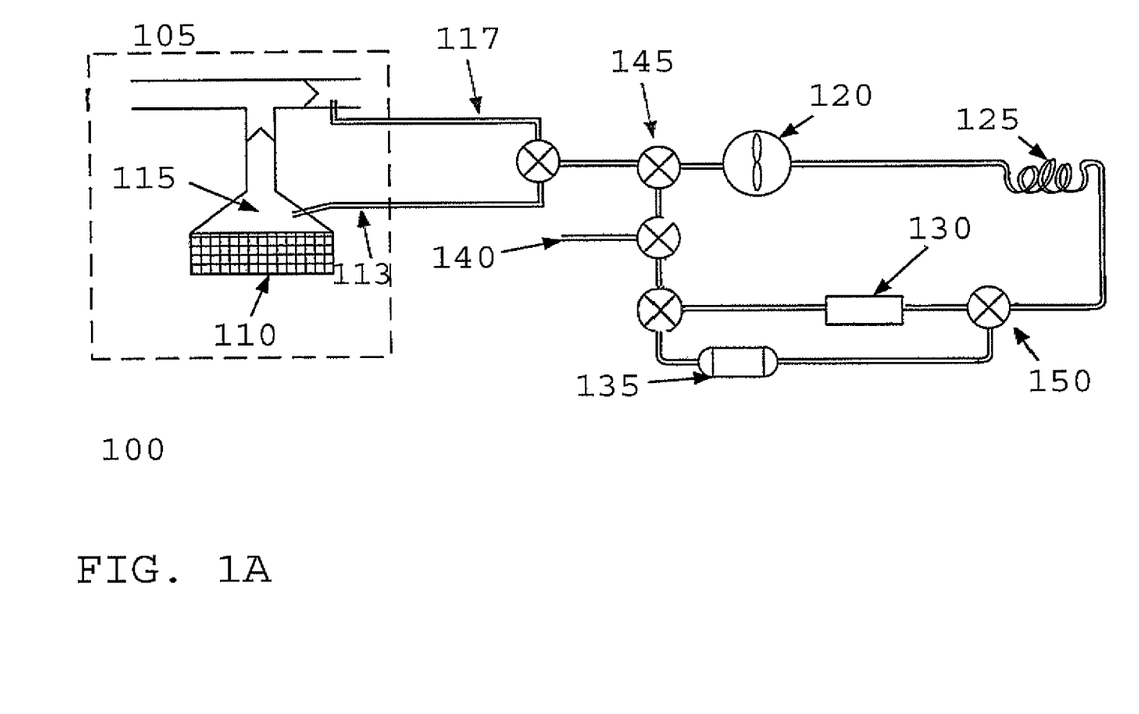
FIG. 1A is a diagram of an apparatus used for sampling breath for the detection of breath analytes.

FIG. 1A is a block diagram of a device 100 that may be used to measure an analyte in exhaled air. As will be described in greater detail below, the device 100 may be configured to circulate the exhaled air through the device multiple times. Each time the exhaled air is circulated through the device, the analyte in the exhaled air is partially converted from a first state to a second state.

According to an embodiment, the device 100 includes a mouthpiece 105. Mouthpiece 105 may be used by a patient to inhale and exhale air. As the patient inhales ambient air, the incoming air passes through a scrubber 110 which removes particles and other unwanted materials from the air. In an embodiment, the scrubber 110 is an NO scrubber which removes particles and NO from the ambient air as it is inhaled.

As a result of being passed through the scrubber 110, the inhaled air is NO free air 115 which is inhaled and subsequently exhaled by the patient. The NO free air 115 may also be delivered directly to the sampling circuit via tube 113 to purge the system prior a sample from the patient. The exhaled air now contains only NO that was present in the patient's lungs. In an embodiment, the scrubber 110 may be any conventional NO scrubber having an inlet, outlet and a filter filled with suitable filtering matter. The mouthpiece may also be configured to contain an antimicrobial filter (not shown) to further ensure that both the inhaled air and exhaled air are clean and free from bacteria and other particles.

The air is exhaled through the mouthpiece 105 and passed to a tube 117. As shown in FIG. 1A, the tube may have a number of different paths that lead to various components of the device 100. In an embodiment, flow down each of the paths and to the various components may be controlled by a one of a plurality valves, such as valve 145. The valves, such as valve 145, may be two way or three way valves depending on the number of intersections of the tube and depending on a flow direction of the exhaled air. The valves may also be configured to allow or restrict the flow of air to the various components and areas of the device 100 at different times and in various circumstances.

Device 100 also includes a pump 120 configured to circulate the exhaled air though the tube 117. In an embodiment, pump 120 may be configured to pump the exhaled air through the tube 117 at various flow rates. The flow rates may be determined on the type of components (e.g., sensor and converter) the device 100 has and how the particular components handle various flow rates.

As the exhaled air is circulated through the tube 117 via the pump 120, a portion of the exhaled air may pass through or be stored in a sample storage tube 125. In an embodiment, the sample storage tube 125 is part of the tube 117 but is configured in a non-linear fashion. For example, the sample storage tube 125 may be configured as a coil as shown in FIG. 1A. In an embodiment where the non-linear coil configuration is used, the overall capacity of the device increases while the size of the device decreases. Because the non-linear portion may be used as temporary storage, a balloon or other component, such as a piston pump, are not necessary for the device 100 to store a sample of exhaled air. Although a coil configuration is shown in FIG. 1A, it is contemplated that many other designs and shapes may be used in place of a coil to essentially increase the internal volume of the flow path. The internal volume will depend upon a number of design features such as the particular sample size, the specific analyte, and the number of times the circulating air will be sampled. In addition, it is also contemplated that more than one non-linear portion, similar to sample storage tube 125, may also be included in the device 100. Alternatively, the sample storage tube may be long and straight having a small diameter with respect to its length. In either embodiment, the diameter of the tube should be narrow and uniform. Such a design helps prevent dilution of the sample air as ambient air is being drawn into the tube while testing of the sample occurs.

According to embodiments, the length and diameter of the sample storage tube depends on the required flow rate and exposure time of the particular sensor used. The following table shows examples of tube length and diameter based on a 10 second minimum sensor exposure time requiring a 10 cc/second sample flow with a 100 cc minimum.

TABLE 1

| Tube Diameter | Volume/Meter | Tube Length (in meters) |
| --- | --- | --- |
| 0.125 | 7.8429 | 12.75039 |
| 0.188 | 17.64653 | 5.666838 |
| 0.250 | 31.3716 | 3.187596 |
| 0.313 | 49.01813 | 2.040062 |
| 0.375 | 70.5861 | 1.41671 |

Although specific values are expressed in the above tables, other volumes, tube lengths and tube diameters may also be used. For example, some sensors may exhaust the analyte in the exhaled breath sample as it flows across the sensor, while other sensors don't. Therefore, a tube with a smaller length may be used when the exhaled breath is recirculated across the sensor multiple times.

Once the exhaled air is stored in the sample storage tube 125, the exhaled air may pass through the tube 117 to valve 150. Valve 150 may be configured to permit the air to pass either to converter 130 or sensor 135. According to an embodiment, the flow path may change at valve 150 depending on whether the analyte is to be converted from one state to another prior to passing through the sensor, or alternatively, whether the sensor is going to receive the exhaled air without the analyte first passing through the converter 130.

When it is determined that the exhaled air is to be passed to converter 130, the valve 150 may open the path to the converter while closing the path to the sensor 135. As the exhaled air passes through the converter 130, the analyte in the exhaled air is partially converted to a different compound or state. In an embodiment, the converter 130 is a catalytic converter configured to convert NO to $NO_2$. In embodiments such as this, the conversion may be necessary because an analyte sensor, such as for example, sensor 135 may be configured to only measure certain compounds (e.g., configured to measure $NO_2$ instead of NO). As the exhaled air is re-circulated through the device 100 and passes through the converter 130, the conversion from the first state to the second state continues.

As can be seen in FIG. 1A, the tube 117 in the device 100 may be configured to allow the flow of the exhaled air to re-circulate through the different paths of the tube and at a rate determined by the pump 120. This particular configuration also enables the converter 130 to operate at a lower efficiency than would otherwise be required if the exhaled air were to pass through the converter only once. Because the air is re-circulated through the tube 117, the converter 130 may partially convert the NO to $NO_2$ the first time the air passes through the converter, and continue the conversion process the second, and third times etc. the analyte passes through the converter 130.

As explained above, each time the analyte in the exhaled air passes through the converter 130, a fraction of the NO is converted to $NO_2$. Thus, the device 100 does not have a need for a high efficiency converter, nor is one required. Because the exhaled air is passed through the device a number of times, a lower efficiency converter can perform the same quality of conversions as the higher efficiency converter.

According to an embodiment, and as stated above, each time the air passes through the converter 130 a fraction of the NO contained in the exhaled air is converted to $NO_2$. This is demonstrated by the formula: $F=(1-(1-e)^n)$ where "e" is the fractional efficiency of the converter and "n" is the number of times the gas is circulated through the converter. For example, if the converter efficiency is 70% and the exhaled air is circulated three times through the device 100, then amount of NO converted to $NO_2$ is 97.3%.

In an embodiment, once the exhaled air has passed through the converter 130 a predetermined number of times, or alternatively, once the exhaled air has been circulating through the device for a minimum or maximum amount of time, valve 150 may be configured to allow flow to pass to sensor 135 while restricting flow to the converter 130. Sensor 135 then measures the levels of the converted analyte in the exhaled breath. In an alternative embodiment, the converted air may be stored in the sample storage tube 125 and then sent to sensor 135 when the sensor is ready to receive the sample. In an alternative embodiment, the valve 150 may restrict flow to the converter 130 when the exhaled air is first received and the flow of the air may proceed directly to the sensor 135.

Although the sensor described herein is configured to detect $NO_2$, it is contemplated that the sensor, and the device, may be configured to convert and/or detect other analytes such as NO, $CO_2$, $NH_3$, $H_2$, CO and the like. Regardless of the analyte being sampled, the sample may be sent to the sensor at a controlled rate, thus providing improved measurement accuracy. In an embodiment, once the sensor has completed the reading, data representing the reading be transmitted to a display device (not shown). The display device may be a physically present on the device 100, such as for example, on an LCD screen (not shown), or alternatively, the data may be transmitted, either by a direct connection or wirelessly to a peripheral display device (not shown).

When the device is finished with the exhaled air, the exhaled air may be discharged through the discharge tube 140.

Figure 1B:
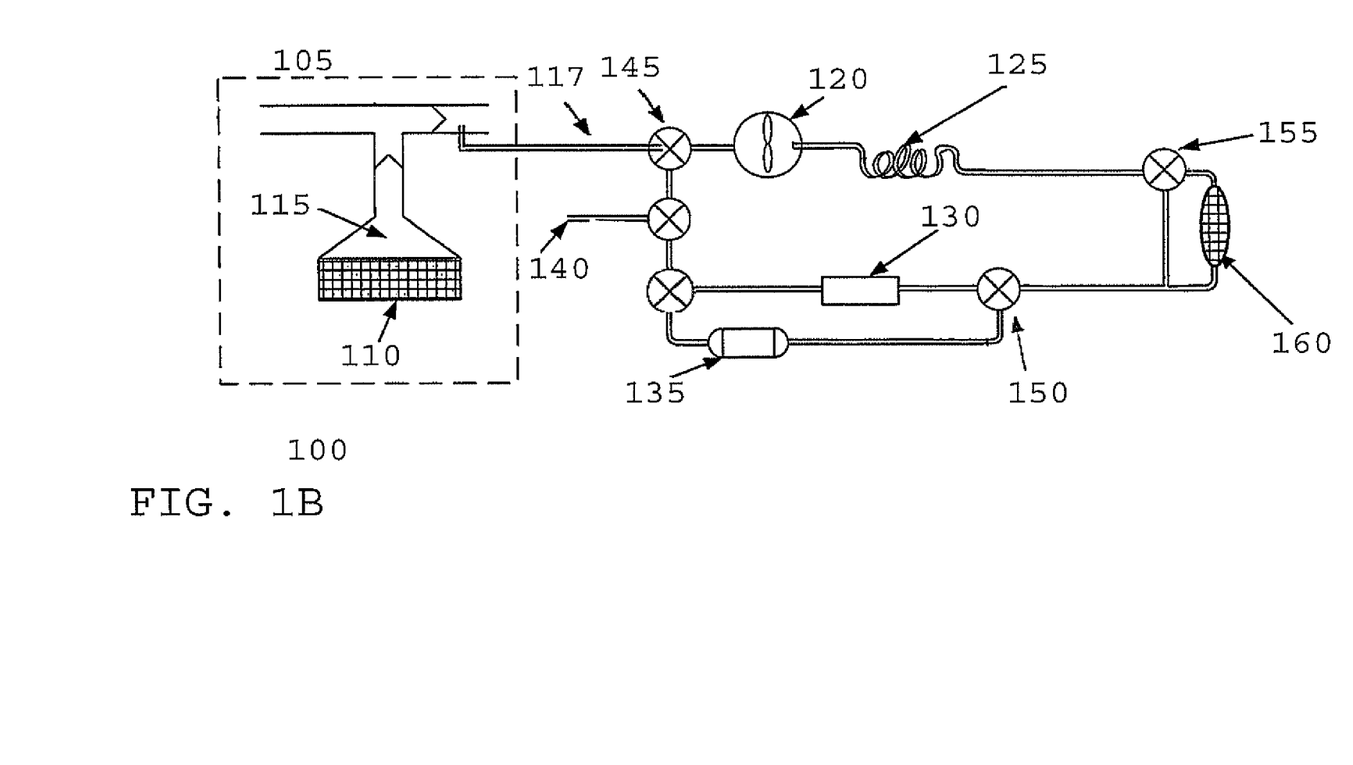
FIG. 1B is another embodiment of an apparatus used for sampling breath for the detection of breath analytes.

FIG. 1B is another embodiment of an apparatus used for sampling breath for the detection of breath analytes.

As shown in FIG. 1B, the configuration of the device 100 is similar to the configuration of the device of FIG. 1A. However, the device of FIG. 1B contains an additional scrubber 160 that may be used to scrub the air for various analytes prior to sending the sample to the sensor 135. In an embodiment, valve 155 controls the flow path of the exhaled air and either allows or denies the exhaled air to enter the scrubber 160. As with scrubber 110, scrubber 160 may be configured to scrub NO, or other analytes, from the exhaled air as the air circulates through the tube 117. As with the embodiments described above, once the exhaled air passes through scrubber 160, the air may be passed either to the converter 130 and re-circulated or passed directly to the sensor 135. Such a configuration may prolong the life of the sensor as it helps to ensure that the only analyte being passed to the sensor is an analyte for which the sensor was made to measure.

In an alternative embodiment, the sensor 135 may be placed directly behind the converter 130 with valve 150 being removed. Such an embodiment still provides for the air to be circulated and converted from NO to $NO_2$ as described above but an immediate reading of the analyte is obtained.

Figure 2:
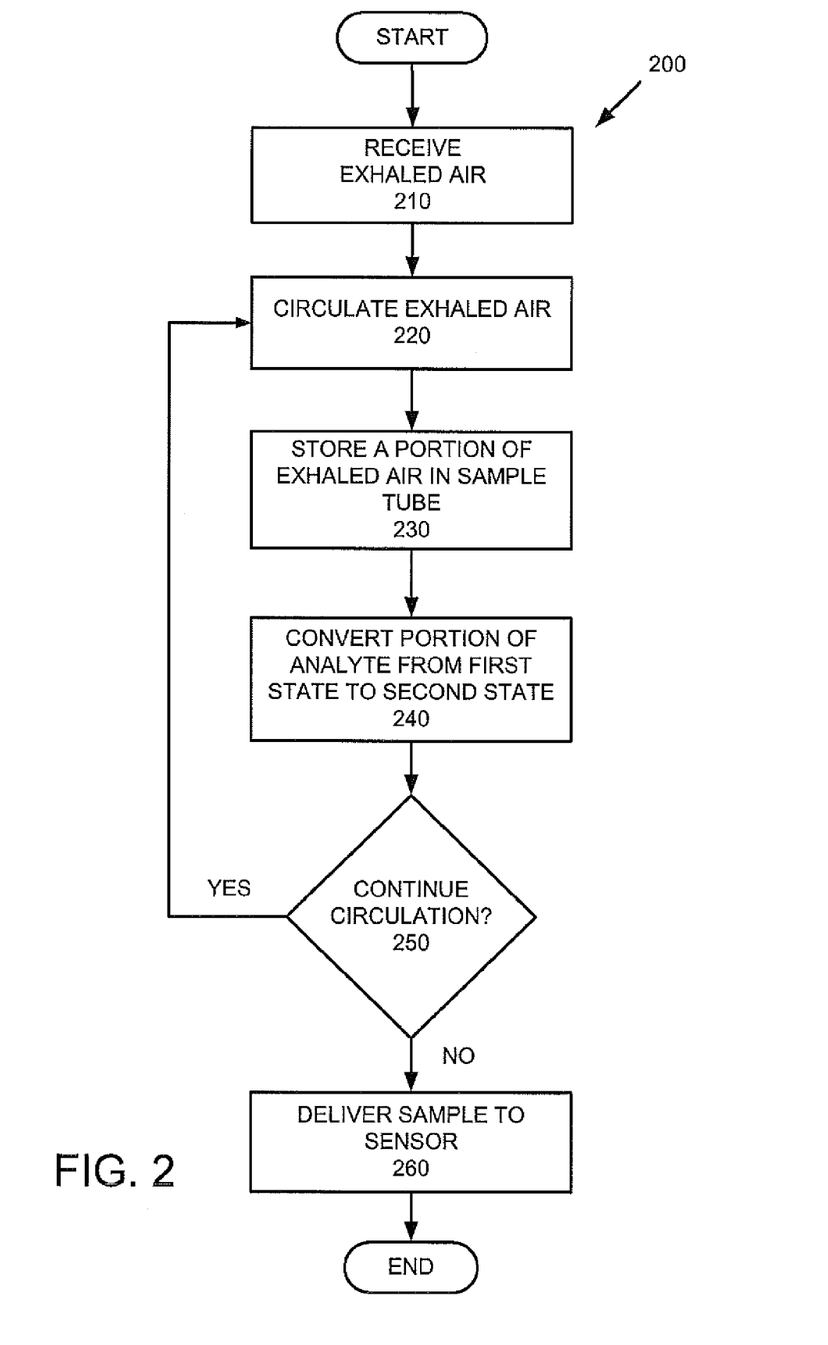
FIG. 2 illustrates a method for measuring levels of an analyte in exhaled breath.

FIG. 2 illustrates a method 200 for measuring levels of an analyte in exhaled air according to an embodiment. The method illustrated in FIG. 2 may be performed in any suitable environment. For example, in environments such as illustrated in FIGS. 1A and/or 1B. Therefore, the description of FIG. 2 may refer to at least one of the components of FIG. 1A or 1B. However, any such reference is for descriptive purposes only, and it is to be understood that the implementations of FIGS. 1A and 1B are non-limiting environments.

According to an embodiment, step 210 provides that exhaled air is received through an inlet tube or mouthpiece. According to an embodiment, the inlet tube or mouthpiece may be the mouthpiece 105 as described above with respect to FIG. 1A. As previously explained, the mouthpiece may contain a scrubber that removes particles and various analytes from the inhaled air. When the inhaled air is exhaled, step 220 provides that the exhaled air is circulated through the device. In an embodiment, the exhaled air is circulated using a circulation pump.

Step 230 provides that the circulated air is stored in a sample storage tube. According to an embodiment the sample storage tube may be configured in a coil and have the capability to store the exhaled air for a period of time. In an embodiment the period of time may be determined by the efficiency rate of the converter and/or a rate at which the sensor can detect the analyte in the exhaled air.

Flow then passes to step 240 which provides that an analyte contained in the exhaled air is partially converted from a first state to a second state. For example, the exhaled air may contain NO. However, the sensor may be configured to only detect $NO_2$. As the exhaled air passes through the converter, the converter changes a fraction of the NO to $NO_2$ thus enabling the sensor to take the desired measurements.

Flow then passes to step 250 where it is determined whether the exhaled air is to be re-circulated. If it is determined that the exhaled air is to be re-circulated, steps 220, 230 and 240 are repeated again with the analyte being further converted from the first state to the second state each time the air passes through the converter.

For example, if on the first cycle, 20% of the analyte is converted from NO to $NO_2$. A determination may be made that the sensor needs a concentration of $NO_2$ to be above a certain threshold (e.g., 90%) before the sensor takes the requested measurement. If it is determined in step 250 that the analyte needs to be further converted, steps 220, 230 and 240 are performed a second, third, or fourth time if necessary. When the re-circulated exhaled air reaches step 240 again, the conversion process continues (e.g., the conversion of the analyte from NO to $NO_2$ is now at 45%).

Once an appropriate threshold has been reached, the decision block 250 branches to "No" and the exhaled air, with the converted analyte, is delivered to the sensor. If however, it is determined that the air must be circulated again, flow passes to "Yes" and the air is delivered to the converter for further conversions.

Step 260 provides that the sample is delivered to the sensor. According to an embodiment, the sample is delivered to the sensor when it is determined the conversion is sufficiently complete. In an alternative embodiment, the exhaled air need not pass through the converter and may be directly sent to the sensor. In yet another embodiment, the exhaled air may be sent to a scrubber, such as scrubber 160 of FIG. 1B, prior to being sent to the converter and/or sensor.

It will be clear that the described device and method are well adapted to attain the ends and advantages mentioned as well as those inherent therein. Those skilled in the art will recognize that the method and device described within this specification may be implemented in many different manners and as such is not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. Numerous other changes may be made which will readily suggest themselves to those skilled in the art and which are encompassed in the spirit of the disclosure and as defined in the appended claims.

What is claimed is:

1. An apparatus for measuring an analyte in exhaled air, the apparatus comprising:
    an inlet through which the exhaled air is received;
    a tube coupled to the inlet, the tube having a plurality of paths and a non-linear portion, the non-linear portion being configured to temporarily store at least a portion of the exhaled air;
    a pump configured to circulate the exhaled air through the tube;
    a converter configured to partially convert the analyte from a first state to a second state; and
    an analyte sensor for measuring the analyte;
    wherein the at least a portion of the exhaled air is temporarily stored in the tube while it is determined whether the at least a portion of the exhaled air will be passed to the converter or the analyte sensor, and wherein the tube is configured to re-circulate the exhaled air through the converter until a percentage of the analyte converted to the second state exceeds a pre-determined threshold.

2. The apparatus of claim 1, where the non-linear portion is configured as a coil.

3. The apparatus of claim 1, wherein the converter is a catalytic converter.

4. The apparatus of claim 1, further comprising one or more valves coupled to the tube, wherein the one or more valves are configured to change a flow path of the exhaled air through the tube from a first path of the plurality of paths to a second path of the plurality of paths.

5. The apparatus of claim 1, wherein the converter is configured to receive the partially converted air at least a second time and perform at least a second partial conversion of the analyte from the first state to the second state.

6. The apparatus of claim 1, wherein the analyte is nitric oxide and the converter is configured to partially convert the nitric oxide to nitrogen dioxide.

7. The apparatus of claim 6, wherein the analyte sensor is configured to measure nitrogen dioxide.

8. An apparatus for measuring an analyte in exhaled air, the apparatus comprising:
    an inlet through which exhaled air is received;
    a tube coupled to the inlet, wherein at least a portion of the tube is configured to store a sample of the exhaled air, the portion of the tube being in a non-linear configuration;
    a pump configured to circulate the exhaled air through the tube; and
    a converter configured to receive the exhaled air at least a first time and a second time, wherein when the exhaled air is received the first time, the converter partially converts the analyte from a first state to a second state and wherein when the analyte is received the second time, the converter further converts the analyte from the first state to the second state, and wherein the sample of the exhaled air is temporarily stored in the tube while it is determined whether the sample of the exhaled air will be passed to the converter, and wherein the tube is configured to re-circulate the exhaled air through the converter until a percentage of the analyte converted to the second state exceeds a pre-determined threshold.

9. An apparatus for measuring an analyte in exhaled breath, the apparatus comprising:
    an inlet through which exhaled air is received;
    a tube coupled to the inlet, the tube having a non-linear portion configured to store the exhaled air;

a converter configured to partially convert the analyte from a first state to a second state; and an analyte sensor for measuring the analyte in the exhaled air, wherein the exhaled air is temporarily stored in the tube while it is determined whether the exhaled air will be passed to the analyte sensor, wherein the tube is configured to re-circulate the exhaled air through the converter until a percentage of the analyte converted to the second state exceeds a pre-determined threshold.

10. The apparatus of claim 9, wherein the converter is a catalytic converter.

11. The apparatus of claim 9, wherein converter partially converts the analyte from nitric oxide to nitrogen dioxide.

12. The apparatus of claim 9, wherein the analyte sensor is configured to measure nitrogen dioxide.

13. The apparatus of claim 9, wherein the non-linear portion is configured as a coil.

* * * * *

UNITED STATES PATENT AND TRADEMARK OFFICE
CERTIFICATE OF CORRECTION

| | | |
|---|---|---|
| PATENT NO. | : 8,652,064 B2 | Page 1 of 1 |
| APPLICATION NO. | : 12/242887 | |
| DATED | : February 18, 2014 | |
| INVENTOR(S) | : Lockett E. Wood, Ron J. Kadlec and John Andrew Battista, Jr. | |

It is certified that error appears in the above-identified patent and that said Letters Patent is hereby corrected as shown below:

Title Page item (75) Inventors, "Ron J. Kadlac" should read --Ron J. Kadlec--.

Signed and Sealed this
First Day of July, 2014

Michelle K. Lee
*Deputy Director of the United States Patent and Trademark Office*